United States Patent [19]

Welstead, Jr. et al.

[11] Patent Number: 5,183,903

[45] Date of Patent: Feb. 2, 1993

[54] UREA FUSION PROCESS FOR THE SYNTHESIS OF 3-PHENOXY-1-AZETIDINECARBOXAMIDES

[75] Inventors: William J. Welstead, Jr., Richmond, Va.; Young S. Lo, Hockessin, Del.

[73] Assignee: A. H. Robins Company, Incorporated, Richmond, Va.

[21] Appl. No.: 798,674

[22] Filed: Nov. 26, 1991

[51] Int. Cl.$^5$ .................................. C07D 205/04
[52] U.S. Cl. ..................... 548/952; 548/953
[58] Field of Search ...................... 548/952, 953

[56] References Cited

U.S. PATENT DOCUMENTS

| | | | |
|---|---|---|---|
| 3,094,518 | 6/1963 | Testa et al. | 548/953 |
| 4,226,861 | 10/1980 | Cale | 548/952 |
| 4,379,151 | 4/1983 | Cale | 548/952 |
| 4,571,393 | 2/1986 | Teng | 514/210 |
| 4,594,189 | 6/1986 | Lo et al. | 548/952 |
| 4,956,359 | 9/1990 | Taylor et al. | 514/210 |

OTHER PUBLICATIONS

March, J. *Advanced Organic Chemistry, Reactions, Mechanisms and Structure*, third edition, John Wiley & Sons, New York, (1985), pp. 376–377.

Erickson, J. Amer. Chem. Soc. 76, 3977–8 (1954) Reactions with Long Chain Amines. II Reactions with Urea.
Davis and Underwood, J. Amer. Chem. Soc. 44, 2595–2604 (1922) The Urea Dearrangement.
Davis, J. Amer. Chem. Soc. 45, 1816–1820 (1923) The Urea Dearrangement II.

*Primary Examiner*—Joseph Paul Brust
*Assistant Examiner*—Jacqueline Haley
*Attorney, Agent, or Firm*—R. F. Boswell, Jr.

[57] ABSTRACT

This invention relates to an improved process for the preparation of 3-phenoxy-1-azetidinecarboxamides of Formula I which are useful

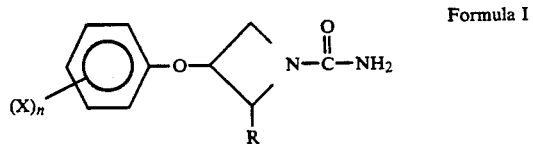

Formula I in the treatment of epileptic seizures. Under Formula I, n is 1 to 3, X is H, halogen, trifluoromethyl, $C_1$–$C_4$ alkyl, $C_1$–$C_4$ alkoxy, acetyl, or aminocarbonyl, and R is H or methyl. This process involves heating a 3-phenoxyazetidine with urea to obtain the Formula I compound. Urea is inexpensive and easily removed by washing the solid Formula I product with water.

11 Claims, No Drawings

UREA FUSION PROCESS FOR THE SYNTHESIS OF 3-PHENOXY-1-AZETIDINECARBOXAMIDES

BACKGROUND OF THE INVENTION

1. Field of Invention

The present invention relates to a process for the synthesis of 3-phenoxy-1-azetidinecarboxamides, particularly 3-(3-trifluoromethylphenoxy)-1-azetidine-carboxamide, in which an appropriately substituted 3-phenoxyazetidine is fused with urea. The compounds prepared by the process of this invention are useful as anticonvulsants.

2. Information Disclosure Statement

Anticonvulsant 3-phenoxy-1-azetidinecarboxamides as shown in Formula I:

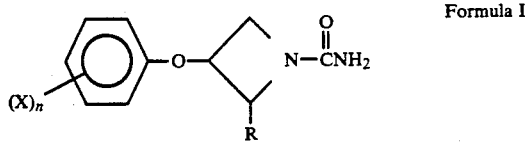

Formula I where n is 1-3, R is H, and X is selected from hydrogen, fluorine, loweralkyl, loweralkoxy, trifluoromethyl, acetyl or aminocarbonyl are disclosed in U.S. Pat. No. 4,571,393. U.S. Pat. No. 4,956,359 further discloses 3-phenoxy-1-azetidinecarboxamides of Formula I in which X, among other things, is chlorine, bromine or iodine and R is H or methyl. The methods of preparation of Formula I carboxamides as disclosed hereinabove involve reaction of a Formula II intermediate where n, X and R

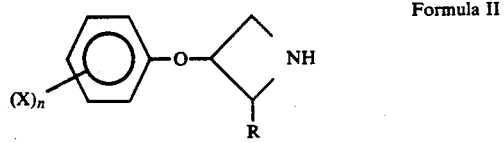

Formula II are as defined under Formula I below with either nitrourea or phosgene/ammonium hydroxide. The reaction with nitrourea involves heating a Formula II compound with nitrourea in an appropriate organic solvent such as ethanol. Nitrourea is relatively expensive, somewhat unstable, and potentially explosive and thus is not the reagent of choice for a large scale reaction. The synthetic procedure involving phosgene requires formation of a 3-phenoxyazetidine-1-carbonyl chloride from a Formula II intermediate followed by reaction of the carbamoyl chloride with ammonium hydroxide. Both phosgene and ammonium hydroxide are toxic and formation of the carbamoyl chloride requires the use of an anhydrous aprotic solvent. The Formula II intermediate is prepared from the N-protected intermediate having the structure shown as Formula III:

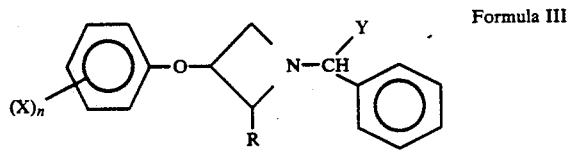

Formula III where n, X and R are as defined under Formula I below and Y is methyl or phenyl by catalytic hydrogenolysis in the presence of an appropriate hydrogenation catalyst to remove the $-CHYC_6H_5$ group. An alternative procedure for preparing the 3-phenoxyazetidine-1-carbonyl chloride is to react a Formula III compound with phosgene, which N-dealkylates the Formula III compound, giving the corresponding carbamoyl chloride and the chlorinated by-product, $ClCHYC_6H_5$ which is a lachrymator and skin and lung irritant. The above synthetic procedures are given in the U.S. patent cited hereinabove and in U.S. Pat. Nos. 4,954,189 and 4,379,151.

Reactions of urea with primary alkylamines to obtain monosubstituted ureas which may be further reacted to give symmetrical dialkylureas, alkylbiurets and dialkylbiurets appear in the literature. T. L. Davis and H. W. Underwood, Jr., J. Amer. Chem. Soc. 44, 2596-2597 (1922) report that no reaction occurs between urea and diphenylamine or N-ethylaniline and that with dibutyl and diamylamines or their hydrochlorides, the formation of a by-product, ammonium chloride, indicated that reaction had taken place, although the products were exceedingly difficult to separate. T. L. Davis and K. C. Blanchard, J. Amer. Chem. Soc. 45, 1817 (1923), report that when an aqueous solution of urea and N-methylaniline hydrochloride or N-ethylaniline hydrochloride was refluxed, the corresponding unsymmetrical ureas were produced in poor yields. J. C. Erikson, J. Amer. Chem. Soc. 76, 3977-8 (1954) reported the synthesis of 1,1-dioctadecylurea from dioctadecylamine and urea heated together at 160°-165° C. for 5 hours.

SUMMARY OF THE INVENTION

This invention concerns a process for the preparation of a compound having the formula:

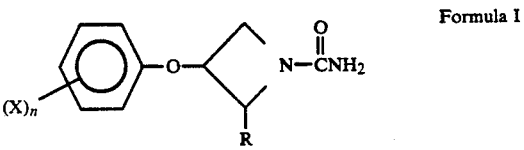

Formula I wherein n is 1 to 3, X is selected from hydrogen, halogen, trifluoromethyl, $C_1-C_4$ alkyl, $C_1-C_4$ alkoxy, acetyl and aminocarbonyl; and R is H or methyl. When n is two or three, the values of X may be the same or different.

The present process obviates the hazards and higher expense associated with nitro-urea or phosgene and comprises heating together a sufficient amount of inexpensive urea and a Formula II compound at a temperature sufficient to drive the reaction to completion. The reaction mixture then is extracted with an organic solvent and/or water to remove any organic impurities and/or unreacted water-soluble urea to obtain the Formula I compound. The reaction proceeds well at temperatures below 150° C. and gives the product in good yield. If the Formula II compound is prepared by catalytic hydrogenolysis to remove the protecting group (i.e., diphenylmethyl or α-methylbenzyl), it is not necessary to remove the diphenylmethane or ethylbenzene formed as the present process provides a method for facile removal of these organic by-products.

DETAILED DESCRIPTION OF THE INVENTION

The process of the invention is summarized in the following reaction scheme:

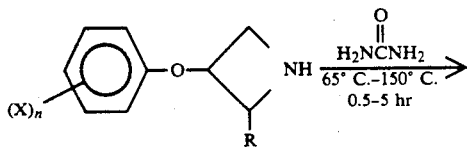

Formula II

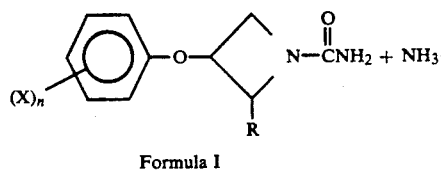

Formula I

In the process of this invention the amount of urea used is from one to ten molar equivalents with respect to the amount of Formula II compound. Preferably the amount of urea used is from one to about two molar equivalents and more preferably, about 1.5 molar equivalents. In general, the urea is added to the Formula II compound at from about 60° C. to about 90° C. The reaction temperature is then raised to a temperature of from about 130° C. to about 150° C. for a period of from 0.5 to 5 hours. When the reaction is complete, the melt is allowed to cool to a lower temperature, ideally from about 80° C. to about 100° C. As noted above, as a "melt" is used, this portion of the process is run in the absence of any solvent.

If diphenylmethane or ethylbenzene is present as a result of the Formula II compound being prepared from 1-(diphenylmethyl or α-methylbenzyl)-3-phenoxyazetidine by catalytic hydrogenolysis to remove the diphenylmethyl or α-methylbenzyl protecting group, the melt is triturated with an organic solvent having a boiling range of from about 80° C. to about 120° C. such as benzene, toluene or petroleum ethers (boiling range 80°-110° C.) or mixtures thereof and the liquid and solid phases separated by conventional means such as filtration or centrifugation. The liquid phase contains the diphenylmethane or ethylbenzene and the solid residue consists of the Formula I compound and unreacted urea, if any.

The solid residue, or melt if diphenylmethane or ethylbenzene is absent, is triturated with water to dissolve any excess urea and the solid Formula I compound is separated from the aqueous urea solution by conventional means, and dried. Further purification is achieved by conventional purification techniques such as recrystallization or chromatography.

The following procedures are illustrative of the process of this invention and are not to be construed as limiting this disclosure in any way.

Urea Fusion Process for the Preparation of
3-(3-Trifluoromethylphenoxy)-1-azetidinecarboxamide Procedure 1

A 30 gallon glass-lined reactor was charged with a solution containing equal parts of 3-(3-trifluoromethylphenoxy)azetidine and diphenylmethane in methanol as obtained from the catalytic hydrogenolysis of 78.32 moles of 1-diphenylmethyl-3-(3-trifluoromethylphenoxy)azetidine. The methanol was distilled off at a pressure of 150 mm Hg until the reactor temperature reached 65° C. The reactor was flushed with nitrogen and charged with 117.4 moles of urea. Heating was continued to approximately 135° C. and held at 135° C. until thin layer chromatographic analysis showed the azetidine derivative to be consumed. When the reaction was complete the mixture was cooled to approximately 80° C. A 30 gallon receiver equipped with an agitator was charged with 80 L of petroleum ether (80°-110° C. boiling range) and the contents of the reactor drained into the receiver with the agitator at high speed. The mixture was slowly cooled to 50° C. and held at that temperature for 5-6 hours. The resulting slurry was then pumped onto a vacuum filter and the filter cake compressed under a rubber dam for 4-5 hours to remove as much solvent as possible.

The filter cake was dried in a vacuum oven at a maximum of 40° C. and the solid then milled to pass through a 100 mesh screen. the receiver was charged with 75 L of water and with agitation charged with the milled solid. After agitating for 4-5 hours, the slurry was pumped onto the vacuum filter. The filter cake was transferred to a vacuum oven and the product dried at 45°-50° C. to obtain 16.45 kg (80%) of the title compound, mp 150°-151.5° C.

Procedure 2

A stirred mixture containing equimolar amounts of 3-(3-trifluoromethylphenoxy)azetidine and diphenylmethane (9.265 kg, 24.1 moles of each) obtained by catalytic hydrogenolysis (Pd/C) was heated to 90° C. under a nitrogen purge while urea (1.445 kg, 24.1 moles) was added. Heating was continued to 137° C. and additional urea (1.445 kg, 24.1 moles) was added portionwise. After 10 minutes at 137° C., nuclear magnetic resonance (nmr) and thin layer chromatographic (tlc) analysis showed the reaction to be only 25% completed. After another 30 minutes, nmr and tlc analysis showed only a trace of starting material. After another 30 minutes, the mixture was cooled to 120° C. Toluene (6 liters) was added and the mixture heated to reflux. The heat was removed and the toluene slurry transferred to a 30 gal glass lined jacketed tank and stirred. The reactor was washed with an additional 3 L of toluene and the wash added to the slurry in the tank. The contents of the tank were chilled by circulating cold (0° C.) ethylene glycol solution in the jacket and heavy crystallization occurred. Petroleum ether (18.6 liters, boiling range 80°-110° C.) was slowly added to the mixture and after 1 hour, stirring was stopped and the mixture allowed to stand overnight. Stirring was then resumed and the slurry pumped onto a 30 gal ceramic filter. The solid was dried under vacuum (product covered with rubber dam) for 2 hours, washed with 3 liters of 1:2 toluene-petroleum ether, and dried under vacuum for another hour. The solid was divided into trays and dried in an oven at 110° F. to obtain 6.17 kg of solid (product and excess urea). The solid was stirred in 24 liters of water for 3 hours and the solid collected by vacuum filtration and dried under a rubber dam for 2 hours. The wet solid was dissolved in 13 liters of hot absolute ethanol, the solution filtered, and 12 liters of warm water (60° C.) added to the filtrate. Seed crystals were added and the solution was chilled in a refrigerator overnight. The recrystallized solid was collected, the cake rinsed with 25% ethanol-75% water, and dried under vacuum at 100° F. for 18 hours to obtain 3.4 kg. The solid was then stirred with 8 liters of isopropyl ether for 2.5 hours, filtered, and the white solid dried at 125° F. overnight to obtain 3.21 kg (61%), of the title compound, mp 151°-152° C.

Analysis: Calculated for $C_{11}H_{11}N_2O_2F_3$: C, 50.77; H, 4.26; N, 10.76. Found: C, 50.81; H, 4.28; N, 10.74.

What is claimed is:

1. A process for the preparation of compound having the formula:

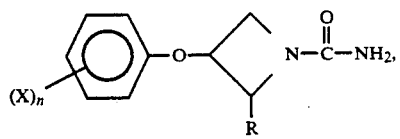

wherein n is 1 to 3, R is H or methyl, and X is hydrogen, halogen, trifluoromethyl, $C_1$-$C_4$ alkyl, $C_1$-$C_4$ alkoxy, acetyl or aminocarbonyl and when n is 2 or 3, the values of X may be the same or different, which comprises heating together a compound having the formula:

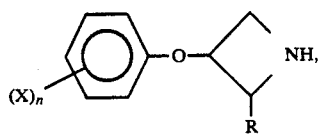

wherein n, X and R are as defined above, with from about 1 to about 10 molar equivalents of urea at from about 60° C. to about 150° C. for from 0.5 to 5 hours in the absence of a solvent.

2. A process according to claim 1 wherein from about 1 to about 10 molar equivalents of urea is admixed with an appropriately substituted 3-phenoxyazetidine at a temperature of from about 60° C. to about 90° C. followed by heating the mixture at a temperature of from about 130° C. to about 150° C. for from 0.5 to 5 hours.

3. A process according to claim 1 in which the reaction mixture, after completion of the reaction, is extracted with water to remove excess urea.

4. A process according to claim 3 in which the reaction mixture, after completion of the reaction, is cooled to a temperature of from about 80° C. to about 100° C. and extracted with water.

5. A process according to claim 1 in which the reaction mixture, after completion of the reaction, is extracted with an organic solvent to remove soluble organic impurities.

6. A process according to claim 5 in which, after completion of the reaction, the mixture is cooled to a temperature of from about 80° C. to about 100° C. and then extracted with an organic solvent to remove soluble organic impurities.

7. A process according to claim 5 in which the organic solvent used is a non-polar, aprotic solvent.

8. A process according to claim 1 in which the reaction mixture, after completion of the reaction, is extracted sequentially with an organic solvent and water to remove soluble organic impurities and urea.

9. A process according to claim 1 wherein the amount of urea used is from about one to about two molar equivalents.

10. A process according to claim 1 wherein n is 1, X is trifluoromethyl and R is hydrogen.

11. A process according to claim 1 wherein n is 1, X is trifluoromethyl, and R is methyl.

* * * * *